United States Patent [19]

Gadient et al.

[11] Patent Number: 5,219,840
[45] Date of Patent: Jun. 15, 1993

[54] ANTIHYPERTENSIVE 9-(2,N6-DISUBSTITUTED ADENYL) RIBOFURANURONIC ACID DERIVATIVES

[75] Inventors: Fulvio Gadient, Birsfelden; Arnold Vogel, Riehen, both of Switzerland

[73] Assignee: Sandoz Ltd., Basle, Switzerland

[21] Appl. No.: 693,891

[22] Filed: May 1, 1991

Related U.S. Application Data

[63] Continuation of Ser. No. 455,662, Dec. 21, 1989, abandoned, which is a continuation of Ser. No. 176,913, Apr. 4, 1988, abandoned.

[30] Foreign Application Priority Data

| | | |
|---|---|---|
| Apr. 6, 1987 [DE] | Fed. Rep. of Germany | 3711561 |
| Apr. 6, 1987 [JP] | Japan | 3711562 |
| Apr. 6, 1987 [JP] | Japan | 3711563 |
| Apr. 6, 1987 [JP] | Japan | 3711564 |

[51] Int. Cl.$^5$ .................. A61K 31/70; C07H 19/167
[52] U.S. Cl. .................. 514/46; 536/27.22
[58] Field of Search .................. 514/45, 46; 536/24, 536/26

[56] References Cited

U.S. PATENT DOCUMENTS 4,167,565 9/1979 Stein et al. .................. 514/46
4,855,288 8/1989 Gadient et al. .................. 514/45

FOREIGN PATENT DOCUMENTS 0094738 10/1987 Japan.
8600310 1/1986 World Int. Prop. O. .

Primary Examiner—Johnnie R. Brown
Assistant Examiner—L. Eric Crane
Attorney, Agent, or Firm—Robert S. Honor; Melvyn M. Kassenoff; Thomas O. McGovern

[57] ABSTRACT $N^6$, 2-disubstituted or 2-substituted 1'-desoxy-1'-(6-amino-9-purinyl)-β-D-ribofuranuronic acid amides, N-substituted amides, N,N-disubstituted amides, thioamides, N-substituted thioamides and N,N-disubstituted thioamides are effective against raised blood pressure.

5 Claims, No Drawings

ANTIHYPERTENSIVE 9-(2,N⁶-DISUBSTITUTED ADENYL) RIBOFURANURONIC ACID DERIVATIVES

This is a continuation of application Ser. No. 07/455,662, filed Dec. 21, 1989, now abandoned, which in turn is a continuation of application Ser. No. 07/176,913, filed Apr. 4, 1988, now abandoned.

The invention relates to new in position 2 substituted 1'-desoxy-1'-(6-amino-9-purinyl)-$\beta$-D-ribofuranuronic acid amides and thioamides, process for their production and their use in the treatment of e.g. raised blood pressure.

The new, in position 2 substituted 1'-desoxy-1'-(6-amino-9-purinyl)-$\beta$-D-ribofuranuronic acid amides and thioamides produced according to the invention are referred to hereinafter as compounds according to the invention.

The compounds may be substituted where desired e.g. in free amino groups.

The invention especially provides in position 2 substituted 1'-desoxy-1'-(6-amino-9-purinyl)-$\beta$-D-ribofuranuronic acid amides and thioamides of formula I

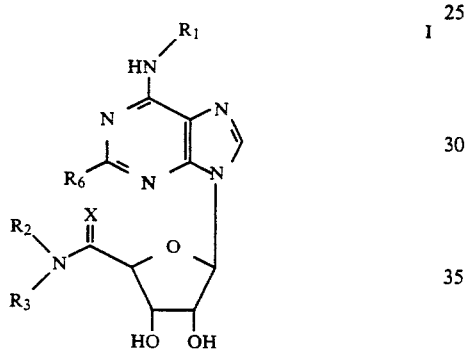

wherein $R_1$ signifies hydrogen, $(C_{1-6})$alkyl which may be optionally monosubstituted by a hydroxyl, a —SH— or a $$-N\begin{matrix}R_4\\R_5\end{matrix}\text{ group,}$$

wherein $R_4$ and $R_5$ signify independently from each other hydrogen or $(C_{1-4})$alkyl; $(C_{3-7})$-alkenyl, $(C_{3-7})$alkinyl, $(C_{3-7})$cycloalkyl which may be optionally mono- or di-substituted by a hydroxyl, a —SH— or a $$-N\begin{matrix}R_4\\R_5\end{matrix}\text{ group,}$$

wherein $R_4$ and $R_5$ are defined as above; $(C_{3-7})$cycloalkyl$(C_{1-3})$alkyl which may be optionally mono- or di-substituted in the cycloalkyl ring by a hydroxyl, a $$-\text{SH}-\text{ or a }-N\begin{matrix}R_4\\R_5\end{matrix}\text{ group,}$$

wherein $R_4$ and $R_5$ are defined as above; phenyl which may be optionally mono- or di-substituted by halogen with an atomic number of 9-35, $(C_{1-4})$alkyl, $(C_{1-4})$alkoxy, a hydroxyl, a —SH— a —S—$(C_{1-4})$alkyl, a —SO$_2$—$(C_{1-})$alkyl, a trifluoromethyl- or $$-\text{SO}_2-N\begin{matrix}R_4\\R_5\end{matrix}\text{ group,}$$

wherein $R_4$ and $R_5$ are defined as above; phenyl-$(C_{1-4})$alkyl which is optionally mono- or di-substituted in the phenyl ring by halogen with an atomic number of 9-35, $(C_{1-4})$alkyl, $(C_{1-4})$alkoxy, a hydroxyl, a —SH—, a —S—$(C_{1-4})$alkyl-, a —SO$_2$($C_{1-4}$)alkyl- or a $$-\text{SO}_2-N\begin{matrix}R_4\\R_5\end{matrix}\text{-group,}$$

wherein $R_4$ and $R_5$ as defined as above, and the $(C_{1-6})$alkylene chain is straight-chain or branched and may be optionally substituted by a hydroxyl group; phenyl-$(C_{3-7})$alkenyl- which may be optionally substituted in the phenyl ring by halogen with an atomic number of 9-35, $(C_{1-4})$alkyl, $(C_{1-4})$alkoxy, a hydroxyl, a —SH—, a —S—$(C_{1-4})$alkyl—, a —SO$_2$—$(C_{1-4})$alkyl- or a $$-\text{SO}_2-N\begin{matrix}R_4\\R_5\end{matrix}\text{ group,}$$

wherein $R_4$ and $R_5$ are defined as above; a 5 or 6 membered, monocyclic heteroaryl which contains one or two nitrogen atoms or one oxygen atom or one sulphur atom and respectively one nitrogen atom; or a 5 or 6 membered, monocyclic heteroaryl-$(C_{1-5})$alkyl containing in the heteroaryl moiety one or two nitrogen atoms or one oxygen atom or one sulphur atom and respectively one nitrogen atom, whereby the alkylene moiety is straight-chain or branched and may be optionally substituted by a hydroxyl group, and $R_2$ signifies hydrogen, $(C_{1-4})$alkyl which may be optionally mono-substituted by a hydroxyl, a —SH— or a $$-N\begin{matrix}R_4\\R_5\end{matrix}\text{ group,}$$

wherein $R_4$ and $R_5$ are defined as above, or it signifies $(C_{3-8})$cycloalkyl, and $R_3$ is hydrogen or $(C_{1-4})$alkyl which may be optionally mono-substituted by a hydroxyl, a —SH— or a $$-N\begin{matrix}R_4\\R_5\end{matrix}\text{ group,}$$

wherein $R_4$ and $R_5$ are defined as above, and $R_6$ is halogen, $(C_{1-4})$alkyl, $(C_{3-5})$cycloalkyl, cyano, or it denotes groups of formulae —OR$_4$, —SR$_4$,

wherein R₄ and R₅ are defined as above and
X signifies =O or =S.

Of the compounds of formula I, preferred compounds possess the formula Ia

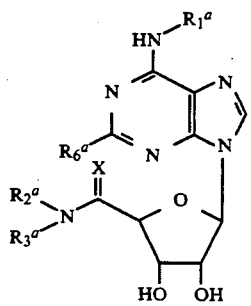

wherein
$R_1^a$ signifies hydrogen, ($C_{1-6}$)alkyl, ($C_{3-7}$)cycloalkyl, which may be optionally mono- or di-substituted by a hydroxyl, a —SH— or a

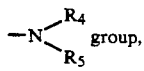

wherein R₄ and R₅ are defined as above; phenyl-($C_{1-6}$)alkyl which may be mono- or di-substituted in the phenyl ring by halogen with an atomic number of 9–35, ($C_{1-4}$)alkyl, ($C_{1-4}$) alkoxy, a hydroxyl, a —SH—, a —S—($C_{1-4}$)alkyl, a —SO₂—($C_{1-4}$)alkyl or a

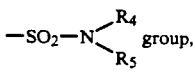

wherein R₄ and R₅ are defined as above, whereby the ($C_{1-6}$)alkylene chain is straight-chain or branched and may be optionally substituted by a hydroxyl group; or phenyl which may be optionally mono- or di-substituted by halogen with an atomic number of 9–35, ($C_{1-4}$)alkyl, ($C_{1-4}$)alkoxy, a hydroxyl, a —SH—, a —S—($C_{1-4}$)alkyl, a —SO₂—($C_{1-4}$)alkyl- a trifluoromethyl- or a

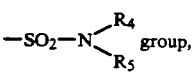

wherein R₄ and R₅ are defined as above,
$R_2^a$ is hydrogen, ($C_{1-4}$)alkyl which may be optionally mono-substituted by a hydroxyl, a —SH— or a

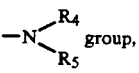

wherein R₄ and R₅ are defined as above; or ($C_{3-6}$)-cycloalkyl, and $R_3^a$ is hydrogen or ($C_{1-4}$)alkyl which may be optionally mono-substituted by a hydroxyl, a —SH— or a

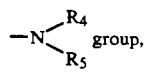

wherein R₄ and R₅ are defined as above, and
$R_6^a$ is halogen with an atomic number of 9–35, ($C_{1-4}$)alkyl or it denotes groups of formulae —OR₄ or

wherein R₄ and R₅ are defined as above and
X denotes =O or =S.

Of the compounds of formula I, especially preferred compounds possess the formula Ib,

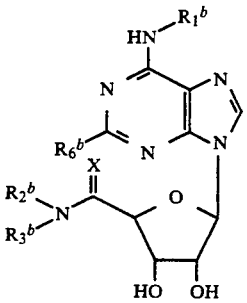

wherein
$R_1^b$ signifies hydrogen, ($C_{1-6}$)alkyl, ($C_{3-7}$)cycloalkyl which may be optionally mono- or di-substituted by a hydroxyl, a —SH— or a

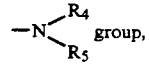

wherein R₄ and R₅ are defined as above; or phenyl which may be optionally mono- or di-substituted by halogen with an atomic number of 9–35, ($C_{1-4}$)alkyl, a ($C_{1-4}$)alkoxy, a hydroxyl, a —SH—, a S-($C_{1-4}$)alkyl, a-SO₂—($C_{1-4}$)alkyl- a trifluoromethyl- or a

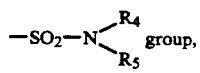

wherein R₄ and R₅ as defined as above,
$R_2^b$ is hydrogen, ($C_{1-4}$)alkyl which may be optionally mono-substituted by a hydroxyl, a —SH— or a

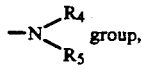

wherein R₄ and R₅ are defined as above; or ($C_{3-6}$)-cycloalkyl and
$R_3^b$ is ($C_{1-4}$)alkyl, and
$R_6^b$ is ($C_{1-4}$)alkyl, chlorine, bromine, methoxy, methylthio, methylamino or dimethylamino and
X denotes =O or =S.

In formula I, halogen with an atomic number of 9–35 denotes fluorine, chlorine or bromine, preferably chlorine, a $(C_{1-4})$alkyl group is methyl, ethyl, n-propyl, i-propyl, n-butyl, i-butyl, tert.-butyl, and if it contains up to 6 carbon atoms, it is also n-pentyl, i-pentyl, 3-pentyl, n-hexyl, i-hexyl, etc. especially methyl, ethyl, isopropyl or 3-pentyl, a $(C_{1-4})$alkoxy group is methoxy, ethoxy, n-propoxy, i-propoxy, n-butoxy, i-butoxy, tert.-butoxy, and if it contains up to 6 carbon atoms, it is also n-pentoxy, i-pentoxy, n-hexoxy, i-hexoxy, etc., especially methoxy, $(C_{3-7})$alkenyl is methallyl, butentyl, pentenyl, etc., whereby the chain may be straight or branched and the double bond may be found in various positions, but not adjacent to nitrogen, $(C_{3-7})$alkinyl is propinyl, butinyl, pentinyl, hexinyl, whereby the chain is straight or branched and the triple bond may be found in various positions, but not adjacent to nitrogen, $(3-7)$-cycloalkyl signifies cyclopropyl, cyclobutyl, cyclopentyl, cyclohexyl or cycloheptyl especially cyclopentyl. If it is substituted, the substituents are respectively in o-, p- or m-position, but appropriately either when disubstituted in o-, o'-position, or when monosubsituted in p-position,. $(C_{3-7})$cyloalkyl$(C_{1-3})$alkyl may denote the above-mentioned cycloalkyl and alkyl radicals, whereby as shown, the substituents may be bonded. Substitution of the phenyl ring may take place in o-, m- or p-position, whereby when disubstituted this is preferably in m- and p-position, and when monosubstituted this is in m or p-position. In phenylalkyl, the alkyl radicals and the substitution of the phenyl ring are as discussed above.

The compounds according to the invention are obtained e.g. by cleavage of an isopropylidene group from in position 2 substituted 1'-desoxy-1'-(6-amino-9-purinyl)-2',3'-isopropylidene-β-D-ribofuranuronic acid amides and thioamides e.g. of formula II

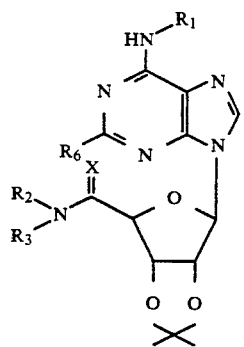

wherein $R_1$, $R_2$, $R_3$, $R_6$ and X have the definitions given above.

The above process conveniently takes place by treating compounds of formula II with an agent which cleaves the isopropylidene group. Trifluoroacetic acid has proved to be especially suitable for this. A further cleavable agent is aqueous hydrochloric acid or aqueous formic acid.

The compounds of formula II used as starting compounds are obtained by introducing an isopropyliden protecting group into compounds of formula III,

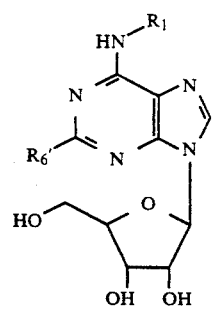

wherein $R_1$ is defined as above and $R_6'$ denotes halogen, $(C_{1-})$alkyl or $(C_{3-5})$cycloalkyl, (described for example in DE-OS 1 670 175; BRIT. PAT 1 075 008 and JOC (1968) 2583), by reacting it with acetone in the presence of an acid, for example p-toluenesulphonic acid, whereby compounds of formula IV

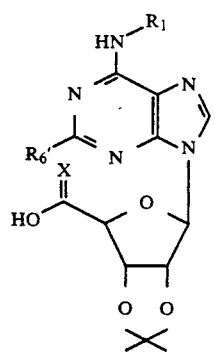

wherein $R_1$ and $R_6'$ are defined as above, are obtained, then oxidising them in known manner to form compounds of formula V,

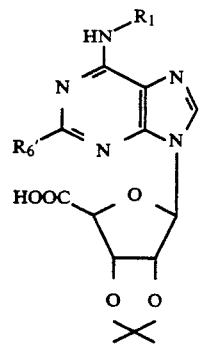

wherein $R_1$ and $R_6'$ are defined as above, using an oxidation agent, for example pyridinium dichromate, and subsequently converting this in known manner, using a chlorination agent such as thionyl chloride, into the acid chloride of formula VI,

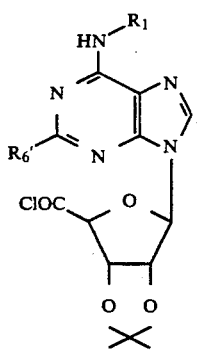

VI wherein $R_1$ and $R_6'$ are defined as above, and then reacting this with a compound of formula VII,

VII wherein $R_2$ and $R_3$ have the definitions given above, in known manner, to form compounds of formula IIa

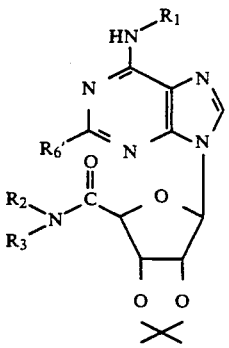

IIa (partial structure of compounds of formula II), wherein $R_1$, $R_2$, $R_3$ and $R_6'$ are defined as above.

The radical $R_6''$, which is defined as below, is introduced into compounds of formula IIa, wherein $R_6'$ is chlorine or bromine, by reacting them with compounds of formula $HR_6'''$ wherein $R_6'''$ denotes a cyano group or groups of formulae —$OR_4$, —$SR_4$ or

wherein $R_4$ and $R_5$ are defined as above, in a strongly alkaline medium, for example in the presence of sodium, or by reacting them with the corresponding amines in an autoclave at temperatures of above 100° C. The compounds of formula IIb

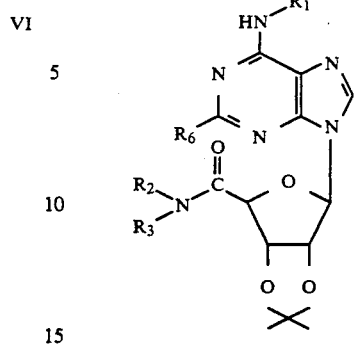

IIb (compounds of formula II, wherein X denotes=O and $R_6$ comprises the significancies of both $R_6'$ and $R_6'''$) wherein $R_1$, $R_2$, $R_3$ and $R_6$ are defined as above which are obtained according to the preceding steps are converted by appropriate thianation into compounds of formula IIc

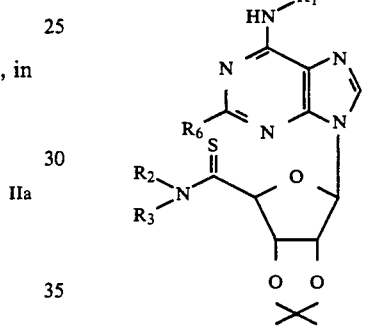

IIc (compounds of formula II, wherein X denotes=S) wherein $R_1$, $R_2$, $R_3$ and $R_6$ are defined as above.

The thianation process is suitably effected using known thianation agents, for example hydrogen sulphide, phosphorus pentasulphide or LAWESSON'S REAGENT (p-methoxyphenylthiophosphine sulphide dimer). The latter reagent is preferred. The reaction itself takes place in known manner. If for example hydrogen sulphide is used, an acid such as hydrochloric acid is conveniently added in catalytic doses, and the reaction is carried out in a polar solvent such as acetic acid or ethanol. When using LAWESSON'S REAGENT, the reaction is conveniently carried out in a dry solvent such as toluene or methylene chloride.

A further method for the production of compounds of formula IIb, wherein $R_6$ is $(C_{1-4})$alkyl, is that 1'-desoxy-1'(2-alkyl-6-hydroxy-9-purinyl)-β-D-ribose of formula IIIa,

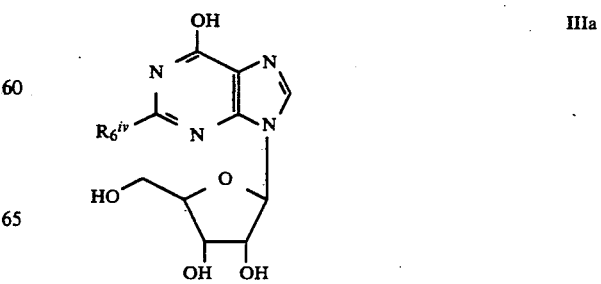

IIIa wherein $R_6^{iv}$ is $(C_{1-4})$alkyl, is reacted with acetone in the presence of an acid, for example p-toluenesulphonic acid, to form compounds of formula IVa,

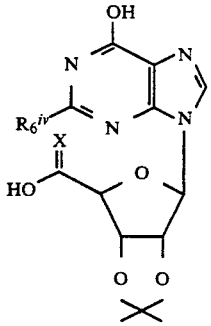

IVa wherein $R_6^{iv}$ is defined as above, then these are oxidised using an oxidation agent, for example potassium permanganate, in an alkaline medium, to produce compounds of formula Va,

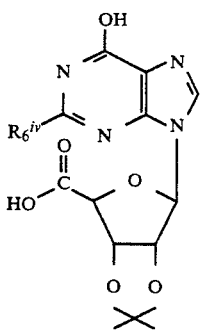

Va wherein $R_6^{iv}$ is defined as above,
then these are treated with a chlorination agent, for example phosphorus oxichloride, thus being converted into compounds of formula VIa,

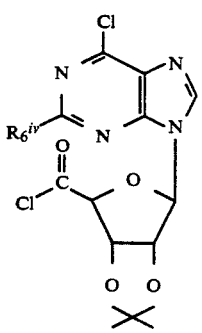

VIa wherein $R_6^{iv}$ is defined as above,
then these are reacted with the above-mentioned compounds of formula VII to produce compounds of formula VIIIa, VIIIa wherein $R_2$, $R_3$ and $R_6^{iv}$ are defined as above, and these are converted by reacting with compounds of formula X, $$R_1-NH_2 \quad\quad X$$

wherein $R_1$ is defined as given above, to form compounds of formula IIb, wherein $R_6$ is $(C_{1-4})$alkyl. The compounds of formula IIb thus obtained, wherein $R_6$ is $(C_{1-4})$alkyl, may be converted by thianation as described above into the corresponding compounds of formula II.

The other above-described reactions take place using known methods, for example also using the processes described in the examples.

If in the compounds of formula I, $R_1$ denotes groups which are substituted by a

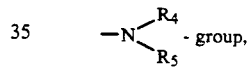 - group, these compounds can form salts with strong acids. Preferred salts are the hydrochlorides, hydrobromides or fumarates.

Insofar as the production of the required starting materials is not described, these are known or may be produced by known processes, or analogousy to the processes described here, or analogously to known processes.

In the following examples, all temperatures are given in degrees celsius and are uncorrected.

EXAMPLE 1

1'-desoxy-1'-(2-methyl-6-cyclopentylamino-9-purinyl)-β-D-ribofuranuronic acid N-ethylamide 1.4 g of 1'-desoxy-1'-(2-methyl-6-cyclopentylamino-9-purinyl)-2',3'-isopropylidene-β-D-ribofuranuronic acid-N-ethylamide are left to stand for 2 hours at 0° and for 1 hour at room temperature in 10 ml of 90% trifluoroacetic acid. The mixture is then totally concentrated under reduced pressure and the residue is partitioned between ethyl acetate and diluted, aqueous ammonia. After washing with saturated, aqueous sodium chloride solution, the product is dried over sodium sulphate and totally concentrated. The residue is dissolved in a little methanol and the final product is crystallised by adding ethylether. M.p. 195°–197°.

The 1'-desoxy-1'-(2-methyl-6-cyclopentylamino-9-purinyl)-2',3'-isopropylidene-β-D-ribofuranuronic acid-N-ethylamide used as the starting material may be produced e.g. as follows:

a) 7.5 g of potassium permanganate are added to a solution of 7.8 g of 1'-desoxy-1'-(2-methyl-6-hydroxy-9-purinyl)-2',3'-isopropylidene-β-D-ribose in 120 ml of water and 4.8 ml of 10N sodium hydroxide, and the mixture is stirred for 1 hour at 30°. Then, 1 g of sodium hydrogen sulphite is added and the colourless solution is filtered over Hyflo after stirring for 5 minutes. The filtrate is then concentrated to ca. 30 ml under reduced pressure, and set at pH 4 with concentrated hydrochloric acid at 0°. 1'-desoxy-1'-(2-methyl-6-hydroxy-9-purinyl)-2',3'-isopropylidene-β-D-ribofuranuronic acid is precipitated in crystalline form. M.p. after washing with acetone and drying: 263° (decomp.).

b) 3.3 g of 1'-desoxy-1'-(2-methyl-6-hydroxy-9-purinyl)-2',3'-isopropylidene-β-D-ribofuranuronic acid are stirred into 16.8 ml of phosphorus oxychloride for 15 minutes in an oil bath of 85°, then mixed with 1.6 ml of N,N-diethylaniline and stirred for a further 2 hours at the same temperature. The mixture is subsequently totally concentrated under reduced pressure and the residue is dissolved in 60 ml of tetrahydrofuran. This solution is cooled to −40° and is mixed with ethylamine until a basic reaction takes place. After 10 minutes, the solution is poured onto ice water and shaken with ethyl acetate. After washing with saturated sodium chloride solution and drying over sodium sulphate, the solution is totally concentrated and the residue is eluted on silica gel with ethyl acetate. The purified 1'-desoxy-1'-(2-methyl-6-chloro-9-purinyl)-2',3'-isopropylidene-β-D-ribofuranuronic acid-N-ethylamide is a white foam and in ethyl acetate has a Rf value of 0.5.

c) 1.2 g of 1'-desoxy-1'-(2-methyl-6-chloro-9-purinyl)-2',3'-isopropylidene-β-D-ribofuranuronic acid-N-ethylamide and 1.2 ml of cyclopentylamine are stirred into 30 ml of dioxane for 1 hour in an oil bath of 105°. After cooling, filtration is effected, the filtrate is concentrated and the residue is eluted on 60 g of silica gel with ethyl acetate. The pure 1'-desoxy-1'-(2-methyl-6-cyclopentylamino-9-purinyl)-2',3'-isopropylidene-β-D-ribofuranuronic acid-N-ethylamide is obtained as a white foam. Rf value in ethyl acetate: 0.45.

The following compounds of formula I, in which $R_1$, $R_2$, $R_3$ and $R_6$ are defined as follows and wherein X is always=O are obtained analogously to example 1:

| Example | $R_1$ | $R_2$ | $R_3$ | $R_6$ | M.P. |
|---|---|---|---|---|---|
| 2 | p-Methoxyphenyl | H | Et | Me | 221–224° |
| 3 | Cyclopentyl | H | Et | Me | 196–198° |
| 4 | Cyclopentyl | H | Et | Isopropyl | amorphous |
| 5 | Cyclopentyl | H | Et | Cl | 133–135° |
| 6 | Cyclopentyl | H | Et | Br | 188–190° |
| 7 | Cyclopentyl | H | Et | MeO | 226–229° |
| 8 | Cyclopentyl | H | Et | MeS | amorphous |
| 9 | Cyclopentyl | H | Et | Me$_2$N | amorphous |
| 10 | Cyclopentyl | H | Et | MeHN | 193–194° |
| 11 | H | H | Et | Br | 240–241° |
| 12 | p-Ethoxyphenyl | H | Et | Me | 120–125° |
| 13 | 3,4-Dimethoxyphenyl | H | Et | Me | 236–239° |
| 14 | 3-Pentyl | H | Et | Me | 181–183° |
| 15 | m-Fluorophenyl | H | Et | Me | 137–142° |
| 16 | p-Fluorophenyl | H | Et | Me | 257–259° |
| 17 | p-Chlorophenyl | H | Et | Me | 255–258° |
| 18 | Isopropyl | H | Et | Me | 187–194° |
| 19 | p-Trifluoromethylphenyl | H | Et | Me | 248–250° |

The 1'-desoxy-1'-(2-chloro-6-cyclopentylamino-9-purinyl)-2',3'-isopropylidene-β-D-ribofuranuronic acid-N-ethylamide also useful as the starting material for the preparation of compounds of formula II wherein $R_6$ has the significance of $R_6'''$ may be produced e.g. as follows:

a) 8.8 ml of ortho-formic acid trimethylester is added in drops at room temperature to 7.4 g of 1'-desoxy-1'-(2-chloro-6-cyclopentylamino-9-purinyl)-β-D-ribose and 4.2 g of p-toluene-sulphonic acid in 120 ml of acetone. After 3 hours, the deposit is filtered off and washed with acetone and diethylether. Then, the dried deposit is added in portions whilst stirring to a solution of 3.6 g of sodium hydrogen carbonate in 150 ml of water and 75 ml of ethyl acetate. The organic phase is separated, washed with saturated sodium chloride solution, dried over sodium sulphate and concentrated.

The oily residue is then purified by eluting on 140 g of silica gel with a mixture of methylene chloride/ethanol 9:1. The pure 1'-desoxy-1'-(2-chloro-6-cyclopentylamino-9-purinyl)-2',3'-isopropylidene-β-D-ribose has a Rf value of 0.5.

b) 8.7 g of 1'-(2-chloro-6-cyclopentylamino-9-purinyl)2',3'-isopropylidene-β-D-ribose and 30.5 g of pyridinium dichromate are stirred for 18 hours at room temperature in 130 ml of dimethylformamide. The mixture is then poured onto water and the aqueous phase is shaken out three times with ethyl acetate. This phase is then extracted with a saturated, aqueous solution of sodium hydrogen carbonate, the basic extract is adjusted to pH 1 with 5N hydrochloric acid and shaken out with ethyl acetate. After washing with saturated sodium chloride solution and drying over sodium sulphate, the organic phase is concentrated, diluted with diethylether, whereby the 1'-(desoxy-1'-(2-chloro-6-cyclopentylamino-9-purinyl)-β-D-ribofuranuronic acid crystallises out. M.p. 246°–253°.

c) 4 g of the above acid are heated in 40 ml of thionyl chloride for 20 minutes in an oil bath of 45°. When the evolution of gas has ended, the mixture is concentrated under reduced pressure and the acid chloride formed is dissolved in 40 ml of methylene chloride. It is then cooled in an ice bath and gaseous ethylamine is introduced whilst stirring until the reaction becomes basic. The methylene chloride phase is then washed with water, dried over sodium sulphate and concentrated. The 1'-desoxy-1'-(2-chloro-6-cyclopentylamino-9-purinyl)-2',3'-isopropylidene-β-D-ribofuranuronic acid-N-ethylamide remains behind as a white foam. Rf in methylene chloride/ethanol 9:1=0.7.

The preparation of compounds of formula II, $R_6$ having the significance of $R_6'''$ and X being =O is performed starting from the above compound of formula IIa wherein $R_6'$ is chlorine in a manner known per se e.g. by reaction with an alcohol, amine etc.

EXAMPLE 20

1'-desoxy-1'-(2'-methyl-6-cyclopentylamino-9-purinyl)-β-D-ribofuranuronic acid-N-ethylthioamide a) 1'-desoxy-1'-(2-methyl-6-cyclopentylamino-9-purinyl)-2',3'-isopropyliden-β-D-ribofuranuronic acid-N-ethylthioamide.

1.7 g of 1'-desoxy-1'-(2-methyl-6-cyclopentylamino-9-purinyl)-2',3'-isopropylidene-β-D-ribofuranuronic acid-N-ethylamide (starting compound of example 1)

are stirred with 0.77 g of LAWESSON'S REAGENT in 38 ml of toluene for 2 hours in an oil bath of 100°. The mixture is subsequently totally concentrated under reduced pressure, the residue is dissolved in 60 ml of ethyl acetate and stirred for ½ hour with 25 g of neutral aluminium oxide. After filtration, the filtrate is concentrated and is used in the next stage without further purification. Rf in ethyl acetate: 0.7.

b) 1'-desoxy-1'-(2-methyl-6-cyclopentylamino-9-purinyl)-β-D-ribofuranuronic acid-N-ethylthioamide.

1.5 g of 1'-desoxy-1'-(2-methyl-6-cyclopentylamino-9-purinyl)-2',3'-isopropylidene-β-D-ribofuranuronic acid-N-ethylthioamide are dissolved at room temperature in 7.5 ml of 90% trifluoroacetic acid and left to stand for 2 hours. The solution is subsequently totally concentrated under reduced pressure. The residue is dissolved in ethyl acetate, mixed with aqueous ammonia and totally concentrated under reduced pressure. The crystalline residue of the compound named in the title, is then purified by eluting on 30 g silica gel with a mixture of methylene chloride/ethanol 9:1. Finally, the pure fractions are crystallised from ethylether/pentane. M.p. 168°-170°.

The following compounds of formula I in which $R_1$, $R_2$, $R_3$ and $R_6$ are defined as follows and wherein X is always=S are obtained analogously to example 20.

| Example | $R_1$ | $R_2$ | $R_3$ | $R_6$ | M.P. |
|---|---|---|---|---|---|
| 21 | 3-Pentyl | H | Et | Me | amorphous |
| 22 | p-Ethoxyphenyl | H | Et | Me | 202-205° |
| 23 | p-Methoxyphenyl | H | Et | Me | 222-225° |
| 24 | 3,4-Dimethoxyphenyl | H | Et | Me | 221-224° |
| 25 | 4-Methylsulfonylphenyl | H | Et | Me | 164-167° |

The compounds according to the invention are notable for their interesting pharmacological properties. They can therefore be used as medicaments.

In particular, the compounds according of the invention have anti-hypertensive activity, as can be deduced from the results of the following trails:

Measurement of the binding to adenosine A1 and A2 receptors in membranes from the rat's cortex or from the cerebral cortex or striatim of the pig, using the method of R. F. BURNS, G. H. LU and T. A. PUGSLEY, which is described in MOLEC. PHARMACOL. 29, 331-346 (1986).

In this binding essay the compounds are active at $A_1$ receptor from 0,1 to 10 mM.

Further testing of the activity of the compounds according to the invention on the isolated, perfused rat's kindneys for the following parameters:
renin secretion
renal haemodynamics (vasodilation)
inhibition of the relates of noradrenaline from the nerve ends following electro-stimulation of the renal nerves according to the method of H. J. SCHUREK, J. P. BRECHT, H. LOHFERT and K. HIERHOLZER, described in COMMUNICATION a la REUNION de l'ASSOCIATION DES PHARMACOLOGISTES LOUVAIN UCL Jun. 4, 1977, as well P. M. VANHOUTTE, D. BROWNING, E. COEN, T. J. VERBEUREN, L. ZONNEKEYEN and M. G. COLLINS described in HYPERTENSION 4, 251-256 (1982).
measurement of blood pressure, heart rate, urine production and renin activity in the plasma of wake, NaCl-depleted, and -replated normotensive or spontaneously hypertensive rates which have catheters implanted in the abdominal aorta and the Vena cava, following i.v. administration or administration of the compounds according to the invention as an infusion or a bolus, according to the method of J. F. M. Smits and J. M. BRODY described in Am. J. Phyiol. 247, R1 003-R1 008 (1984).

From the results of the trails, it can be deduced that both an inhibition of renin secretion and of the release of noradrenaline from the nerve ends, and direct vasodilation, take part in the anti-hypertensive activity of the compounds according to the invention.

The compound of the example the blood pressure in rats in dosages from 0.1 to 1 mg/kg. The preferred compounds are those of examples 1, 2, 5, 11, 14, 15 and 20 especially of examples 1, 2, 5 and 11.

From this, it is evident that the compounds according to the invention can not only be used as anti-hypertensive agents, but can also effect coronary vasodilation. They protect further the vascular endothelium by inhibiting platelet aggregation and by activating leucocytes. They reduce also the blood lipid level.

For the above indications of the compounds according to the invention, the compound of example 2 is preferred.

For the above-mentioned application as anti-hypertensive agents, the dosage to be used varies according to the substance used, the type of administration and the desired treatment. In general however, satisfactory results are obtained with a daily dosage of approximately 0.01 to 10 mg per kg body weight; if necessary, administration may take place in 2 to 4 portions or even in sustained release from. For large mammals, the daily dosage is in the range of approximately 10 to 500 mg; suitable dosage forms for e.g. oral or non-oral administration generally contain about 5 to 250 mg, together with solid or liquid carrier substances.

The compounds according to the invention may be administered alone or in suitable dosage form. The medicinal forms, e.g. a solution or a tablet, can be produced analogously to known methods.

The invention therefore relates also to medicaments which contain the compounds according to the invention in free form or in the form of their physiologically acceptable salts, as well as the production of these medicaments in known manner. They can be produced by using conventional pharmaceutical adjuvants and carriers.

What we claim is:

1. A compound of the formula:

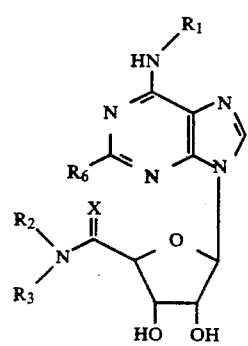

wherein

R₁ signifies $(C_{1-6})$alkyl; $(C_{3-7})$cycloalkyl which is unsubstituted or mono-substituted by a hydroxyl group; or phenyl which is unsubstituted or mono- or di-substituted by halogen with an atomic number of 9-35, $(C_{1-4})$alkyl, $(C_{1-4})$alkoxy, hydroxy or trifluoromethyl, R₂ signifies hydrogen, $(C_{1-4})$alkyl or $(C_{3-8})$cycloalkyl, R₃ is hydrogen or $(C_{1-4})$alkyl, R₆ is halogen, $(C_{1-4})$alkyl, —OR₄, or —SR₄, wherein R₄ is $(C_{1-4})$alkyl and X signifies =S.

2. A compound of the formula

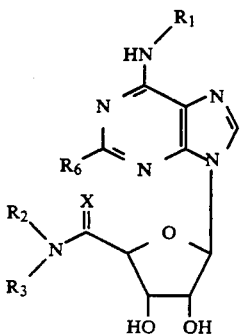   I wherein

R₁ signifies $(C_{1-6})$alkyl; $(C_{3-7})$cycloalkyl which is unsubstituted or mono-substituted by a hydroxyl group; or phenyl which is unsubstituted or mono- or di-substituted by halogen with an atomic number of 9-35, $(C_{1-4})$alkyl, $(C_{1-4})$alkoxy, hydroxy or trifluoromethyl, R₂ signifies hydrogen, $(C_{1-4})$alkyl or $(C_{3-8})$cycloalkyl, R₃ is hydrogen or $(C_{1-4})$alkyl, R₆ is $(C_{1-4})$alkyl, —OR₄, or —SR₄, wherein R₄ is $(C_{1-4})$alkyl, and X signifies =O.

3. A compound selected from:
a) 1'-Desoxy-1'-(2-methyl-6-cyclopentylamino-9-purinyl)-β-D-ribofuranuronic acid-N-ethylthioamide;
b) 1'-Desoxy-1'-(2-methyl-6-cyclopentylamino-9-purinyl)-β-D-ribofuranuronic acid-N-ethylamide;
c) 1'-Desoxy-1'-(2-ethyl-6-cyclopentylamino-9-purinyl)-β-D-ribofuranuronic acid-N-ethylamide;
d) 1'-Desoxy-1'-(2-isopropyl-6-cyclopentylamino-9-purinyl)-β-D-ribofuranuronic acid-N-ethylamide;
e) 1'-Desoxy-1'-(2-methyl-6-p-methoxyphenylamino-9-purinyl)-β-D-ribofuranuronic acid-N-ethylamide;
f) 1'-Desoxy-1'-(2-methylthio-6-cyclopentylamino-9-purinyl)-β-D-ribofuranuronic acid-N-ethylamide;
g) 1'-Desoxy-1'-(2-methoxy-6-cyclopentylamino-9-purinyl)-β-D-ribofuranuronic acid-N-ethylamide;
h) 1'-Desoxy-1'-(2-methyl-6-p-ethoxyphenylamino-9-purinyl)-β-D-ribofuranuronic acid-N-ethylamide;
i) 1'-Desoxy-1'-(2-methyl-6-(3,4-dimethoxyphenyl)amino-9-purinyl)-β-D-ribofuranuronic acid-N-ethylamide;
j) 1'-Desoxy-1'-(2-methyl-6-(3-pentyl)-amino-9-purinyl)-β-D-ribofuranuronic acid-N-ethylamide;
k) 1'-Desoxy-1'-(2-methyl-6-m-fluorophenylamino-9-purinyl)-β-D-ribofuranuronic acid-N-ethylamide;
l) 1'-Desoxy-1'-(2-methyl-6-p-fluorophenylamino-9-purinyl)-β-D-ribofuranuronic acid-N-ethylamide;
m) 1'-Desoxy-1'-(2-methyl-6-p-chlorophenylamino-9-purinyl)-β-D-ribofuranuronic acid-N-ethylamide;
n) 1'-Desoxy-1'-(2-methyl-6-isopropylamino-9-purinyl)-β-D-ribofuranuronic acid -N-ethylamide;
o) 1'-Desoxy-1'-(2-methyl-6-p-trifluoromethylphenylamino-9-purinyl)-β-D-ribofuranuronic acid-N-ethylamide;
p) 1'-Desoxy-1'-(2-methyl-6-(3-pentyl)-amino-9-purinyl)-β-D-ribofuranuronic acid-N-ethylthioamide;
q) 1'-Desoxy-1'-(2-methyl-6-p-ethoxyphenylamino-9-purinyl)-β-D-ribofuranuronic acid-N-ethylthioamide;
r) 1'-Desoxy-1'-(2-methyl-6-p-methoxyphenylamino-9-purinyl)-β-D-ribofuranuronic acid-N-ethylthioamide; and
s) 1'-Desoxy-1'-(2-methyl-6-(3,4-dimethoxyphenyl)-amino-9-purinyl)-β-D-ribofuranuronic acid-N-ethylthioamide.

4. Pharmaceutical composition containing as an active agent a compound of any one of the claims 1, 2 or 3 in association with a pharmacologically acceptable adjuvant and/or diluent useful for the treatment of raised blood pressures.

5. A method of treatment of a raised blood pressure which comprises administering to a subject in need of such a treatment a therapeutically effective amount of a compound of formula I according to claim 1, 2 or 3.

* * * * *